United States Patent [19]

Hunter et al.

[11] Patent Number: 4,742,090
[45] Date of Patent: May 3, 1988

[54] BISMUTH/CARBOXYLIC ACID CATALYSTS FOR PREPARING ELASTOMERS

[75] Inventors: Douglas L. Hunter; David E. Schiff, both of Lake Jackson, Tex.

[73] Assignee: The Dow Chemical Company, Midland, Mich.

[21] Appl. No.: 846,441

[22] Filed: Mar. 31, 1986

[51] Int. Cl.$^4$ ............................................. C08G 18/14
[52] U.S. Cl. ...................................... 521/124; 528/55
[58] Field of Search ........................... 521/124; 528/55

[56] References Cited

U.S. PATENT DOCUMENTS 4,556,703 12/1985 Megna et al. .......................... 528/49
4,584,362 4/1986 Leckart et al. ....................... 528/55
4,611,044 9/1986 Meyer et al. ......................... 521/124

OTHER PUBLICATIONS

Cosan Chemical Corporation "Coscat 83", 1979.
"Cast Urethane Elastomers from Polypropylene Glycols" Rubber Age/vol. 88, No. 3, Dec. 1960.
"A Comparison of Diphenylene Diisocyanate (MDI) and Toluidine Diisocyanate (TDI) Urethane Prepolymers" Plastics & Rubber New, Jan. 1979.

Primary Examiner—Maurice J. Welsh

[57] ABSTRACT

This invention is a polyurethane-urea elastomer which is the reaction product of a reaction mixture comprising (1) a liquid active hydrogen-containing composition which comprises a relatively high equivalent weight active hydrogen-containing compound, and an amine-terminated, relatively low equivalent weight compound, (2) a polyisocyanate which is present in an amount to provide about 0.8 to about 1.5 isocyanate groups per active hydrogen-containing group present in the mixture, and (3) a catalytically effective amount of a bismuth carboxylate catalyst.

With the use of the bismuth carboxylate catalyst, excellent pot-life, yet rapid cures are achieved. In addition the so-called "green strength" of the elastomer, i.e., its physical strength at the time of its removal from the mold, is improved with the practice of this invention. Further, the post-cured elastomer exhibits excellent properties.

28 Claims, No Drawings

BISMUTH/CARBOXYLIC ACID CATALYSTS FOR PREPARING ELASTOMERS

BACKGROUND OF THE INVENTION

This invention relates to the preparation of polyurethane-urea elastomers.

Polyurethane-urea elastomers are often prepared by reacting a relatively high equivalent weight active hydrogen-containing material and a relatively low equivalent weight active hydrogen-containing material (hereinafter "chain extender") with a polyisocyanate. In preparing the elastomer, the reactive components and any catalysts or other optional additives are blended and then transferred to a mold of suitable shape where the formulation is cured. It is typical practice to only cure the elastomer in the mold until it is capable of maintaining its shape, and then demolding the elastomer and postcuring it until the poymerization is completed. In this manner, the molds can be used more often, permitting higher production.

Since it is usually desirable to produce as many parts as possible in a given period of time, it is desirable that the residence time in the mold be as short as possible. A short residence time permits the mold to be used more often in a given time period. Accordingly, it is desirable that the elastomer formulation cure relatively rapidly in the mold to a state at which the elastomer can be demolded and postcured. Conversely, it is necessary that the formulation not cure too quickly, since some time is required to blend the components of the formulation and transfer the blend to the mold.

In conventional practice, particularly with conventional casting techniques using amine chain extenders, no catalyst is used. In such instances, typical in-mold residence times range from about 1 to about 5 hours, depending on the particular components used and the cure temperature. However, in order to decrease energy usage and increase productivity, it is desirable to provide an elastomer formulation which cures more quickly at a lower mold temperature. A common target for preparing elastomers is a 30 minute residence time at about 100°-130° C.

The problems of selecting a catalyst are further complicated when the chain extender is amine-terminated and the high equivalent weight active hydrogen-containing material is hydroxyl-terminated. Amine groups are generally more reactive with isocyanates than are hydroxls, so their presence tends to shorten the pot-life of the elastomer formulation. In addition, although the aforementioned catalysLs catalyze both the hydroxyl-/isocyanate and amine/isocyanate reactions, certain types of these catalysts are more specific for one of these reactions than another. It has thus been difficult to obtain optimal properties from elastomers prepared using these catalysts.

Accordingly, it would be desirable to provide a polyurethane-urea formulation which has a suitable pot-life, cures rapidly to a demoldable state, exhibits minimal degraditive oxidation and which provides an elastomer having desirable physical properties.

SUMMARY OF THE INVENTION

This invention is a molded polyurea or polyurethane-urea elastomer which is the reaction product of a reaction mixture comprising (1) a liquid active hydrogen-containing composition which comprises a relatively high equivalent weight hydroxyl-containing compound, and an amine-terminated, relatively low equivalent weight compound, (2) a polyisocyanate which is present in an amount to provide about 0.8 to about 1.5 isocyanate groups per active hydrogen-containing group present in the mixture, and (3) a catalytically effective amount of a bismuth carboxylate catalyst.

In another aspect, this invention is a liquid active hydrogen-containing composition comprising a relatively high equivalent weight hydroxyl-containing compound, an amine-terminated, relatively low equivalent weight compound and a catalytically effective amount of a bismuth carboxylate.

It has surprisingly been found with the use of the bismuth carboxylate catalyst that excellent pot-life, yet rapid cures are achieved. In addition, the so-called "green strength" of the elastomer, i.e., its physical strength at the time of its removal from the mold, is improved with the practice of this invention. Further, the post-cured elastomer exhibits desirable physical and dynamic properties. An additional advantage is that due to the lower curing temperatures which can be used with this invention, discoloration of the elastomer due to oxidation of certain amine chain extenders is reduced or eliminated.

DETAILED DESCRIPTION OF THE INVENTION

The catalyst used in this invention comprises a bismuth carboxylate. The carboxylate portion of the catalyst advantageously comprises a $C_2$–$C_{30}$, saturated or unsaturated carboxyl terminated hydrocarbyl or inertly substituted hydrocarbyl chain. By inertly substituted, it is meant that the hydrocarbyl chain contains no substituent group which undesirably effects the catalytic behavior of the catalyst. The carboxylate portion of the catalyst is also preferably soluble or miscible with the reaction mixture used in preparing the elastomer. Preferably, the carboxylate portion of the catalyst contains from about 6 to about 22 carbon atoms. Suitable such carboxylate groups include the ions of the so-called fatty acids, as well as branched carboxylates such as neodecanoic acid, Versatic 911 Acid and the like.

The catalyst may contain an excess of carboxylic acid, i.e. the acid may not be completely neutralized with bismuth ions. Advantageously, the catalyst contains about 0.05 to about 25 percent by weight bismuth, based on the weight of the bismuth and the organic portion of the catalyst.

In preparing the elastomer, an active hydrogen-containing composition is reacted with a polyisocyanate. The active hydrogen-containing composition contains as one critical component an relatively low equivalent weight compound having at least two primary or secondary groups per molecule. The equivalent weight of this "chain extender" is advantageously between 30 and about 400, preferably about 30 to about 250. The chain extender also preferably contains about 2 to about 4, more preferably about 2, primary aromatic amine groups per molecule. More preferably, the chain extender contains alkyl or halogen groups in at least one position ortho to each aromatic amine group. Examples of such preferred and more preferred chain extenders include phenylene diamine, toluene diamine, the 2,4- and 2,6- isomers of diethyltoluenediamine, 4,4'-methylene dianiline, methylene bis-(orthochloroaniline), 1,2-bis (2-aminophenylthio)ethane, trimethylene glycol-dip-aminobenzoate, methylene dianthraniline diesters, and the like.

In addition to the chain extender, the active hydrogen-containing composition contains a relatively high equivalent weight compound which contains an average of at least two, preferably 2-4 hydroxyl groups per molecule. The relatively high equivalent weight compound also advantageously has an equivalent weight from about 400 to about 10,000, preferably about 500 to about 3000, more preferably about 750 to about 2000.

Various compounds and polymers can be employed as the relatively high equivalent weight active hydrogen-containing compound. Suitable such materials are described, for example, in U.S. Pat. No. 4,394,491, incorporated herein by reference. Preferred are the polyether polyols, and polyester polyols, with hydroxyl-terminated polymers of ethylene and/or propylene oxide being especially preferred. Minor amounts of relatively high equivalent weight amine-terminated materials, particularly amine-terminated polyethers, can also be employed in the reaction mixture.

The relatively high equivalent weight hydroxyl-containing compound is present in an amount such that mixtures thereof with the chain extender are liquid at ambient temperatures. Preferably, the chain extender comprises about 10 to about 80, preferably about 15 to about 60, more preferably about 20 to about 50 percent by weight of the mixture. Such mixtures are described, for example, in Axelrood and Frisch, "Cast Urethane Elastomers from Polypropylene Glycols", *Rubber Age*, vol. 88, pp. 465-471 (1960).

As is well known in the art, the use of higher amounts of chain extender tends to cause the formation of stiffer elastomers with better high temperature properties. Accordingly, it will be obvious to one skilled in the art to vary the chain extender level to achieve an elastomer of desired properties.

The active hydrogen-containing composition is reacted with a polyisocyanate in the presence of the catalyst described before. Suitable polyisocyanates include aliphatic organic polyisocyanates as well as aromatic organic polyisocyanates. Such polyisocyanates are described, for example, in U.S. Pat. Nos. 4,065,410, 3,401,180, 3,454,606, 3,152,162, 3,492,330, 3,001,973, 3,394,164 and 3,124,605, all incorporated herein by reference.

Especially suitable aromatic polyisocyanates include 2,4- and/or 2,6-toluenediisocyanate, 2,4' and/or 4,4'-diphenylmethanediisocyanate (MDI). p-phenylenediisooyanate, polymethylenepolyphenyl-polyisocyanates, mixtures thereof and the like. Also useful are polymeric derivatives of MDI containing biuret and/or carbodiimide linkages.

Useful aliphatic polyisocyanates include the hydrogenated derivatives of the foregoing aromatic polyisocyanates, as well as hexamethylene diisocyanate, isophorone diisocyanate, 1,4-cyclohexane diisocyanate and the like.

In addition, prepolymers and quasi-prepolymers of the foregoing polyisocyanates having a free —NCO content of about 0.5 to about 32% by weight are useful herein. The use of such prepolymers is generally preferred. Preferably, the prepolymer contains about 2-25% by weight of isocyanate groups, more preferably about 4-18%, most preferably 4-14%, by weight of isocyanate groups. These prepolymers are readily prepared by reacting a stoichiometric excess of the polyisocyanate with an active hydrogen-containing material.

The active hydrogen-containing material can be of high or low equivalent weight, and can be the same or different than the materials used in the active hydrogen-containing composition which is reacted with the polyisocyanate. Preferably, however, the active hydrogen-containing material used in preparing the prepolymer comprises a relatively high equivalent weight polyether having a plurality of hydroxyl or primary or secondary amine groups.

The polyisocyanate and active hydrogen-containing composition are reacted together at proportions such that there are provided about 80 to about 150, preferably about 95-110, isocyanate groups per 100 active hydrogen-containing groups in the reaction mixture.

The catalyst described before is employed in the reaction mixture in any amount which measurably increases the rate of reaction of the reaction mixture. However, it is preferred to employ about 0.001 to about 1, more preferably about 0.01 to about 0.3, part of the catalyst per 100 parts of the polyisocyanate. Above this range, the pot life of the reaction mixture is short, making it difficult to mix the components and fill the mold. At lower levels, the catalytic activity is very slight, and only minimal advantage is obtained by using the catalyst.

In addition to the foregoing critical components, various additives are often advantageously employed in the reaction mixture. Suitable such additives include blowing agents, surfactants, fillers, fibers, pigments, mold release agents (internal or external), antioxidants, dyes and the like.

Suitable filler materials include inorganic fillers such as kaolin or wollastonite clays, calcium carbonate, alum, flaked or milled glass and the like. Suitable fibers include fiberglass, including nonwoven mats, needlepunched mats, chopped fibers and the like; polyester, polyamide and other polymeric fibers, metallic fibers, metal coated polymeric fibers, graphite fibers and the like.

Suitable pigments include carbon black, titanium dioxide, iron oxide, organic dyes and the like.

The elastomer of this invention is preferably noncellular or microcellular (i.e., preferably has a density of at least about 0.8 g/cc). Accordingly, it is preferred to omit a blowing agent or to use a blowing agent only in small quantities which provide a density of about 0.8 g/cc or higher, preferably about 1.0 g/cc or higher. Such blowing agents include air, inert gases such as nitrogen, argon or helium, and compounds which vaporize or react to form a gas under the conditions of the reaction of the polyisocyanate and the active hydrogen-containing composition. Such compounds include water, halogenated alkanes, the so-called "azo" blowing agents and the like.

When a blowing agent is employed, it is often preferable to employ a small quantity of a surfactant, preferably a silicone surfactant which is compatible with the reaction mixture, to stabilize the forming cells against collapse until the reaction mixture is cured.

Conventional casting methods, wherein all components are blended and then transferred into a mold for curing, are suitably used herein. In addition, reaction injection molding (RIM) processing can be employed to prepare an elastomer according to this invention. In either case, improvements in the dynamic properties of the resulting elastomer are seen with this invention. However, the improvements of reduced cure temperature and/or reduced in-mold residence time, as well as that of improved green strength, are most evident when the elastomer has an in-mold residence time of about 1 to about 90 minutes, preferably about 5 to about 60 minutes, more preferably about 15 to about 45 minutes. In particular, the advantages of this invention are especially seen when the chain exntender comprises an aromatic diamine having a reactivity similar to that of methylene bis(orthochloroaniline).

In conventional casting techniques, the components are advantageously mixed at ambient or a slightly elevated temperature before transfer into the mold. Since the active hydrogen-containing composition of this invention often has a relatively high viscosity, it may be beneficial to heat it to about 40°–80° C. to reduce its viscosity, and then to mix it with the polyisocyanate, which itself is maintained at about ambient temperature. The resulting mixture typically has a temperature of about 25°–40° C. (depending on the relative weights of the components). Such temperature provides a reduction in viscosity relative to ambient temperature, but does not cause the components to react rapidly. In conventional casting techniques, the blended components are placed into a suitable mold where they is cured under pressure at an elevated temperature. Suitable post-curing conditions include a termperature of about 70° to about 150° C. and a post cure time of about 1 to about 20 hours. However, post-curing is not required if curing is completed in the mold.

Typical RIM conditions include preheating the components to a temperature of about 25°–80° C., an in-mold residence time of about 1 to about 30, preferably about 1 to about 15 minutes, and a mold temperature of about 70°–150° C., preferably about 100°–130° C.

A distinct advantage of this invention is that at demold, the elastomer has significantly improved "green strength" as compared to a similar elastomer prepared in the same manner except no catalyst, or an organotin, organoiron, organomercury, organic acid and/or tertiary amine catalyst is used. "Green strength" refers to the ability of the elastomer to resist tearing at demold. It is conveniently measured by a "dog-ear" test wherein one corner of the elastomer is bent over 180 degrees, and the crease is inspected for cracks and breakage. Good green strength is indicated by no cracking or very minimal cracking. When green strength is poor, the elastomer will break, crumble or show substantial cracking on this test.

On differential mechanical thermal analysis the elastomer of this invention also usually shows a remarkably small fluctuation in storage modulus over a broad temperature range, and shows a small tan delta (E"/E') value, indicating minimized polymer heat buildup during dynamic use.

The following examples are provided to illustrate the invention, but are not intended to limit the scope thereof. All parts and percentages are by weight unless otherwise indicated.

EXAMPLE 1

An isocyanate terminated prepolymer is prepared by reacting an excess of an 80/20 mixture of 2,4'- and 2,6'-toluenediisocyanate with a 2000 equivalent weight ethylene oxide-capped poly(propylene oxide triol) (Polyol A) to form a prepolymer having an —NCO content of 8.3% by weight (equivalent weight of 506). To 60 parts of this prepolymer are added 0.03 parts of a bismuth salt of neodecanoic acid (commercially available from Cosan Chemical Corporation as Coscat 83 catalyst). To this mixture are added 36 parts of a blend of 40 weight percent methylene bis(o-chloroaniline) and 60 weight percent of Polyol A. The mixture is stirred for about one minute and cast into a suitable preheated mold, where it is cured for 30 minutes at 100° C. The part is then demolded and green strength measured according to the dog-ear test described before. The green strength is as reported in Table 1 following (Sample No. 1). The part is then post-cured for 16 hours at 100° C.

For comparison, various other catalysts are tried in place of the bismuth salt in the same formulation (Comparative Sample Nos. A–H). The curing regime is the same in all cases. The green strength obtained with the use of these catalysts is as reported in Table 1 following.

In Table 1, the following rating system is used, with a 4 rating being best:
1—crumbles on demold
2—material cracks on slight bending on dog ear test
3—material cracks only on substantial bending on dog ear test
4—material exhibits minimal or no cracking on dog ear test

TABLE 1

| Sample No. | Catalyst Type | Catalyst Concentration[1] | Green Strength At Demold | Cooled |
|---|---|---|---|---|
| 1 | Coscat 83[2] Acid | 0.05% | 3 | 4 |
| A* | None | — | 1 | 1 |
| B* | DBTDL[3] | 0.05% | 1 | 2 |
| C* | Cocure 44[4] | 0.13% | 1 | 2 |
| D* | Ferric Acac[5] | 0.1% | 1 | 3 |
| E* | Oleic Acid | 0.1% | 1 | 2 |
| F* | DBTDL/Oleic Acid[6] | 0.05/0.1 | 1 | 3 |
| G* | Cocure 44/O.A.[7] | 0.05/0.05 | 1 | 3 |
| H* | Ferric Acac/O.A.[8] | 0.1/0.1 | 1 | 3 |

*Not an example of this invention
[1]Based on weight of the prepolymer
[2]A bismuth salt of neodecanoic acid
[3]DBTDL = dibutyltindilaurate
[4]An organomercury catalyst
[5]Ferric Acetylacetonate
[6]A mixture of an organotin catalyst and oleic acid
[7]A mixture of an organomercury catalyst and oleic acid
[8]A mixture of ferric acetylacetonate and oleic acid As can be seen from Table 1, significantly better green strength is obtained with the use of this invention.

EXAMPLE 2

An isocyanate-terminated prepolymer is prepared by reacting an excess of an 80/20 mixture of 2,4- and 2,6-toluene diisocyanate with a Polyol A to form a prepolymer having an —NCO content of 8.0% by weight (equivalent weight of 506). To 60 parts of this prepolymer are added 0.03 parts of a bismuth salt of neodecanoic acid (commercially available from Cosan Chemical Corporation as Coscat 83 catalyst). To this mixture are added 36 parts of a blend of 40 weight percent methylene bis(o-chloroaniline) and 60 weight percent Polyol A. The mixture is stirred for about one minute and cast into a suitable preheated mold, where it is cured for 30 minutes at 100° C. The part is then demolded and green strength measured according to the dog-ear test described before. The green strength is rated as a "3" on the scale indicated in Example 1. The part is then post-cured at 100° C. for 16 hours. The postcured part (designated Sample No. 2) has a uniform appearance. The postcured part is evaluated on a Polymer Laboratories Dynamic Mechanical Thermal Analyzer operated at 10

Hertz at a temperature ramp of 4° C./min. The results of this testing are reported in Table 2 following.

The foregoing experiment is repeated, this time omitting the catalyst. The part (Comparative Sample No. I) is rated as a "1" on the dog-ear test before postouring. The postcured test has a mottled appearance and shows areas of incomplete curing. The dynamic mechanical thermal analysis testing of the postcured part is as indicated in Table 2.

As a further comparison, Comparative Sample No. I is repeated, except in-mold curing is done at 150° C. for 1 hour in order to attempt to overcome the lack of catalyst. This sample is designated Comparative Sample No. J. The green strength of the demolded part is rated as a "3". After postcuring, the part has a mottled appearance and exhibits areas of inadequate cure. The dynamic mechanical thermal analysis of the postcured part is as summarized in Table 2.

TABLE 2

| Sample No. | 1 | G* | H* |
|---|---|---|---|
| LOG E' modulus (Pa) | | | |
| 30° C. | 7.6 | 7.7 | 7.4 |
| 150° C. | 7.6 | 7.6 | 7.25 |
| E"/E' (tan delta) | | | |
| 30° C. | 0.09 | 0.15 | 0.14 |
| 150° C. | 0.10 | 0.135 | 0.14 |

*Not an example of this invention.

The data provided in Table 2 indicates that over the temperature range from 30° to 150° C., the sample prepared according to this invention exhibited a substantially lower tan delta value than the Comparative Samples. This indicates that the part will be significantly less susceptible to heat build-up in a dynamic application, and would be expected to have a longer useful life. The storage modulus (E') values indicate that the sample of this invention has excellent stiffness, and retains that value over a wide temperature range.

What is claimed is:

1. A polyurethane-urea elastomer which is the reaction product of a reaction mixture comprising (1) a liquid active hydrogen-containing composition which comprises a relatively high equivalent weight active hydrogen-containing compound, and an amine-terminated, relatively low equivalent weight compound, (2) a polyisocyanate which is present in an amount to provide about 0.8 to about 1.50 isocyanate groups per active hydrogen-containing group present in the mixture, and (3) a catalytically effective amount of a bismuth carboxylate catalyst.

2. The elastomer of claim 1 wherein said amine-terminated relatively low equivalent weight active hydrogen-containing compound contains an average of about 2 aromatic amine groups per molecule.

3. The elastomer of claim 2 wherein said relatively high equivalent weight active hydrogen-containing compound comprises a hydroxyl-terminated polyether.

4. The elastomer of claim 3 wherein said polyether has an equivalent weight of about 500 to about 3000.

5. The elastomer of claim 1 wherein said bismuth carboxylate comprises, as the organic portion of the catalyst, a carboxylate of a C-6 to C-22 carboxylic acid.

6. The elastomer of claim 5 wherein said bismuth carboxylate comprises a bismuth salt of neodecanoic acid.

7. The elastomer of claim 5 wherein said bismuth carboxylate contains about 0.05 to about 25 percent by weight bismuth.

8. The elastomer of claim 7 wherein said active hydrogen-containing composition comprises about 15 to about 60 percent by weight of an aromatic diamine having an equivalent weight from about 31 to about 250, and about 40 to about 85 percent of a polyether polyol having an equivalent weight of about 500 to about 3000, or mixture thereof.

9. The elastomer of claim 8 wherein the aromatic diamine comprises methylene bis(o-chloroaniline), 1,2 bis(2-aminophenylthio)ethane, methylenedianthralilic diesters or trimethylene glycol-di-p-aminobenzoate.

10. The elastomer of claim 1 wherein said polyisocyanate is a aromatic polyisocyanate.

11. The elastomer of claim 5 wherein said polyisocyanate is an aromatic polyisocyanate.

12. The elastomer of claim 9 wherein said polyisocyanate is an aromatic polyisocyanate.

13. The elastomer of claim 1 wherein said polyisocyanate is a prepolymer prepared in the reaction of an excess of an aromatic polyisocyanate and a relatively high equivalent weight hydroxyl terminated polyether.

14. The elastomer of claim 5 wherein said polyisocyanate is a prepolymer prepared in the reaction of an excess of an aromatic polyisocyanate and a relatively high equivalent weight hydroxyl terminated polyether.

15. The elastomer of claim 9 wherein said polyisocyanate is a prepolymer prepared in the reaction of an excess of an aromatic polyisocyanate and a relatively high equivalent weight hydroxyl terminated polyether.

16. A liquid active hydrogen-containing composition comprising (a) a relatively high equivalent weight polyol, (b) an aromatic amine chain extender and (c) a catalytically effective amount of a bismuth carboxylate.

17. The composition of claim 16 comprising about 40 to about 85 percent, based on the weights of components (a) and (b), of a polyether polyol, about 15 to 60 percent of methylene bis(o-chloroaniline), 1,2-bis(2-aminophenylthio)ethane, methylenedianthralilic diesters or trimethylene glycol-di-p-aminobenzoate, and about 0.01 to about 0.3 parts, per 100 parts of components (a) and (b), of a bismuth carboyxlate.

18. The composition of claim 17 wherein the bismuth carboxylate comprises bismuth neodecanoate.

19. The elastomer of claim 1 wherein the elastomer has a density of at least about 0.8 g/cc.

20. A process for forming a polyurethane-urea elastomer by reacting a reaction mixture comprising (1) a liquid active hydrogen-containing composition which comprises a relatively high equivalent weight active hydrogen-containing comound, and an amine-terminated, relatively low equivalent weight compound, having at least two primary or secondary groups per molecule, (2) a polyisocyanate which is present in an amount to provide about 0.8 to about 1.50 isocyanate groups per active hydrogen-containing group present in the mixture, and (3) a catalytically effective amount of a bismuth carboxylate catalyst.

21. The process of claim 20 wherein said relatively high equivalent weight active hydrogen-containing compound comprises a hydroxyl-terminated polyether.

22. The process of claim 20 wherein said polyether has an equivalent weight of about 500 to about 3000.

23. The process of claim 20 wherein said bismuth carboxylate comprises, as the organic portion of the catalyst, a carboxylate of C-6 to C-22 carboxylic acid.

24. The process of claim 20 wherein said active hydrogen-containing composition comprises about 15 to 60 percent by weight of an aromatic diamine having an equivalent weight from about 30 to about 250, and about 40 to about 85 percent of a polyether polyol having an equivalent weight of about 500 to about 3000, or mixture thereof.

25. The process of claim 24 wherein the aromatic diamine comprises methylene bis(o-chloroaniline), 1,2 bis(2-aminophenylthio)ethane, methylenedianthralilicidesters or trimethylene glycol-di-p-aminobenzoate.

26. The process of claim 20 wherein the reaction mixture is reacted in a mold.

27. The process of claim 26 wherein there is an in-mold residence time of from about 1 to about 90 minutes.

28. The process of claim 27 wherein the in-mold residence time is from about 15 to about 45 minutes.

* * * * *